United States Patent
Dib et al.

(10) Patent No.: US 6,720,318 B2
(45) Date of Patent: Apr. 13, 2004

(54) COMBINATION OF CYAMEMAZINE AND AN ATYPICAL NEUROLEPTIC

(75) Inventors: Michel Dib, Paris (FR); Cyrille Leperlier, Fontainebleau (FR)

(73) Assignee: Aventis Pharma S. A., Antony Cedex (FR)

( * ) Notice: Subject to any disclaimer, the term of this patent is extended or adjusted under 35 U.S.C. 154(b) by 0 days.

(21) Appl. No.: 10/164,771

(22) Filed: Jun. 7, 2002

(65) Prior Publication Data

US 2002/0183312 A1 Dec. 5, 2002

Related U.S. Application Data

(63) Continuation of application No. PCT/FR00/03446, filed on Dec. 8, 2000.

(30) Foreign Application Priority Data

Dec. 10, 1999 (FR) .............................................. 99 15632

(51) Int. Cl.[7] ............... A61K 31/5415; A61K 31/5513; A61K 31/519
(52) U.S. Cl. ..................... 514/226.2; 514/220; 514/258
(58) Field of Search ............................. 514/226.2, 220, 514/258

(56) References Cited

U.S. PATENT DOCUMENTS

| | | | |
|---|---|---|---|
| 4,804,663 A | 2/1989 | Kennis | |
| 4,831,031 A | 5/1989 | Lowe | |
| 5,229,382 A | 7/1993 | Chakrabarti | |

FOREIGN PATENT DOCUMENTS

| | | |
|---|---|---|
| EP | 0196132 | 10/1986 |
| EP | 0200322 | 11/1986 |
| EP | 0392959 | 10/1990 |
| EP | 0454436 | 10/1991 |
| EP | 0529500 | 3/1993 |
| EP | 0586191 | 9/1994 |
| EP | 0733634 | 9/1996 |
| FR | 2722099 | 1/1996 |
| WO | WO 94/25460 | 11/1994 |
| WO | 96/30375 | 10/1996 |
| WO | WO 98/43646 | 10/1998 |
| WO | WO 99/16313 | 8/1999 |

OTHER PUBLICATIONS

Vanel et al., Eur. J. Clin. Pharmacol. (55, No. 9, 659–65, 1999) (abstract).*
Dietch, James T. et al., Aggressive Dyscontrol in Patients Treated with Benzodiazepines, J. Clin Psychiatry (1988, pp. 184–188, vol. 49:5).
Overall, John E. et al., The Brief Psychiatric Rating Scale, Psychological Reports, (1962, pp. 799–812, vol. 10).
Senninger, J. L. et al., La Risperidone Dans Le Traitement de L'Agressivite Des Schizophrenes, Ann. Med. Psychol. (1998, pp. 210–213, vol. 156 No. 3).
Stimmel, Glen L., Benzodiazepines in Schizophrenia, Supplement to Pharmacotherapy (1996, pp. 148–151, vol. 16).
Warneke, Lorne B., Benzodiazepines: Abuse and New Use, Can. J. Psychiatry (1991, pp. 194–205, vol. 36).
Wolkowitz, Owen M. et al., Benzodiazepines in the Treatment of Schizophrenia; A Review and Reappraisal, Am J Psychiatry (1991), pp. 714–726, vol. 148:6).
Zini, R et al., The Influence of Various Drugs on the Binding of Tianeptine to Human Plasma Proteins, International Journal of Clinical Pharmacology, Therapy and Toxicology (1991, pp. 64–66, vol. 29 No. 2).

* cited by examiner

Primary Examiner—Phyllis G. Spivack
(74) Attorney, Agent, or Firm—Balaram Gupta

(57) ABSTRACT

The present invention relates to the combination of cyamemazine and an atypical neuroleptic, olanzapine or risperidone, or a pharmaceutically acceptable salt thereof, and to the use thereof in the treatment of schizophrenia, and in particular, of acute episodes of schizophrenia.

14 Claims, No Drawings

COMBINATION OF CYAMEMAZINE AND AN ATYPICAL NEUROLEPTIC

This application is a continuation of International application No. PCT/FR00/03,446, filed Dec. 8, 2000; which claims the benefit of priority of French Patent Application No. 99/15,632, filed Dec. 10, 1999.

The present invention relates to the combination of cyamemazine and an a typical neuroleptic, or a pharmaceutically acceptable salt thereof, and to the use thereof in the treatment of schizophrenia, and in particular of acute episodes of schizophrenia.

Cyamemazine, or cyamepromazine (TERCIAN®), in the form of a base or of a pharmaceutically acceptable salt, and in particular the tartrate thereof, is a neuroleptic of the phenothiazine type (U.S. Pat. No. 2,877,224), which is used in the symptomatic treatment of anxiety in all its forms and which may optionally be combined with an antidepressant in conditions of serious depression.

Atypical neuroleptics, also called a typical antipsychotics, are neuroleptics which produce little or no extrapyramidal side effects.

Among commercially available a typical neuroleptics, mention may be made of the following products:

risperidone (RISPERDAL®) and the pharmaceutically acceptable salts thereof, and in particular the pamoate (patents EP 0 196 132, U.S. Pat. No. 4,804,663 and WO 94/25460);

olanzapine (ZYPREXA®) and the pharmaceutically acceptable salts thereof (EP 0 454 436 and U.S. Pat. No. 5,229,382); and in particular the pamoate (WO 99/16313), the polymorph forms thereof and in particular form II (WO 96/30375) and the solvated forms thereof (EP 0 733 634 and EP 0 831 097).

Other a typical neuroleptics are in the process of being developed; among these, mention may be made of:

sertindole and the pharmaceutically acceptable salts thereof (EP 0 200 322 and EP 0 392 959);

quetiapine and the pharmaceutically acceptable salts thereof (EP 0 240 228);

ziprasidone and the pharmaceutically acceptable salts thereof (U.S. Pat. No. 4,831,031) and the monohydrate thereof (EP 0 586 191).

These products are currently recommended in the front line treatment of schizophrenia. Their effectiveness on positive and negative symptomology and also on the profile of tolerance (lack of or fewer extrapyramidal effects) constitute therapeutic progress for patients.

However, clinical observation shows that, for many schizophrenic patients, the establishment of a neuroleptic treatment of the a typical class does not provide a rapid clinical response, although this is a particularly critical period: anguish with agitation, aggressiveness, behavioral disorders possibly endangering the patient and the medical staff.

The use of benzodiazepines as an associated sedative treatment has been proposed, but their value remains limited (low percentage of responders, need for high doses) and their side effects remain not insignificant (paradoxical sedation or excitation, risk of dependency, of withdrawal and of abuse) (Wolkowitz, O. M., Pickar, D., Am. J. Psychiatry 148, 714–26 (1991); Dietch, J. T., Jennings, R. L., J. Clin. Psychiatry, 49, 184–88 (1988); Warneke, L. B., Can. J. Psychiatry, 36, 194–205 (1991); Glen L. Stimmel, Pharmacotherapy, 16(6Pr 2), pp. 148–151)(1996)).

It has now been found that, in these patients, combining an a typical neuroleptic with cyamemazine allows a clear and rapid therapeutic effect to be obtained on anxiety, tension, aggressiveness and excitation, with very good tolerance and a decrease in schizophrenic symptomology which is, overall, more rapid. This synergistic action may promote patient compliance by rapidly improving their disorders.

This effect was determined on a group of 15 patients who were schizophrenic according to DSM IV (JD Guelfi et al., Masson Paris: 1008p (1996)) and hospitalized.

In a first control group, 7 patients were treated with an a typical neuroleptic alone: 5 patients with 10 to 20 mg/day of olanzapine, taken in a single dose, and 2 patients with 4 to 8 mg/day, taken in 2 doses, for 6 weeks.

In a second group, 8 patients were treated with a combination of cyamemazine and an a typical neuroleptic:

5 patients with 10 to 20 mg/day of olanzapine, taken in a single dose, and 150 mg/day of cyamemazine, taken in 2 doses, for 6 weeks;

3 patients with 4 to 8 mg/day of risperidone, taken in 2 doses, and 150 mg/day of cyamemazine, taken in 2 doses, for 6 weeks.

In the groups treated with the combination, the patients did not experience any behavioral disorders during the hospitalization and half the patients exhibited a decrease of at least 40% in the BPRS (Brief Psychiatric Rating Scale) score (Overall J. E., Gorham D. R., Psychol. Rep., 10:799–812 (1962)) during the first 3 weeks of treatment, which was not observed in the group treated with an a typical neuroleptic alone.

Tolerance (extrapyramidal signs and akathisia) proved to be comparable in all the groups.

These results demonstrate that the combination of an a typical neuroleptic and cyamemazine has a synergistic effect in the treatment of schizophrenic disorders, and these are of very great value in clinical practice.

According to the invention, it is understood that the combinations may comprise a second a typical neuroleptic.

The atypical neuroleptics mentioned above and cyamemazine may be in the form of a pharmaceutically acceptable salt, and in particular in the form of an addition salt with inorganic acids, such as hydrochloric acid, hydrobromic acid, sulphuric acid, phosphoric acid or nitric acid, or organic acids, such as acetic acid, propionic acid, succinic acid, oxalic acid, benzoic acid, fumaric acid, maleic acid, methanesulfonic acid, isethionic acid, theophyllineacetic acid, pamoic acid, salicylic acid, phenolphthaleinic acid, methylene-bis-β-oxynaphthoic acid, carbonic acid, citric acid, lactic acid or palmitic acid, or any of the pharmaceutically acceptable substitution derivatives thereof.

Among these combinations, preference is given to combinations of cyamemazine and olanzapine, of cyamemazine and olanzapine in pamoate form, of cyamemazine and olanzapine in the form of its form II polymorph, of cyamemazine and risperidone, and of cyamemazine and risperidone in pamoate form.

The combination may be used orally, parenterally or rectally, either simultaneously or separately or in a manner spread out over time.

The present invention also relates to the pharmaceutical compositions comprising the combination of cyamemazine and an a typical neuroleptic in the pure state or in the form of a combination with one or more compatible and pharmaceutically acceptable diluents and/or adjuvants, and/or optionally in combination with another pharmaceutically compatible and physiologically active product.

Tablets, pills, powders (gelatine capsules, cachets) or granules may be used as solid compositions for oral administration.

In these compositions, the active principles are mixed with one or more inert diluents, such as starch, cellulose, sucrose, lactose or silica, under a stream of argon. These compositions may also comprise substances other than the diluents, for example one or more lubricants, such as magnesium stearate or talc, a dye, a coating (dragées) or a varnish.

Liquid compositions which may be used for oral administration include pharmaceutically acceptable solutions, suspensions, emulsions, syrups and elixirs containing inert diluents such as water, ethanol, glycerol, plant oils or paraffin oil. These compositions may comprise substances other than the diluents, for example wetting, sweetening, thickening, flavoring or stabilizing products.

The sterile compositions for parenteral administration may preferably be aqueous or nonaqueous solutions, suspensions or emulsions. Solvents or vehicles which may be used include water, propylene glycol, a polyethylene glycol, plant oils, in particular olive oil, and injectable organic esters, for example ethyl oleate or other suitable organic solvents. These compositions may also contain adjuvants, in particular wetting agents, isotonic agents, emulsifiers, dispersants and stabilizers. The sterilization may be carried out in several ways, for example by aseptic filtration, incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semisynthetic glycerides or polyethylene glycols.

The present invention also relates to the use of a combination of cyamemazine and an a typical neuroleptic, or a pharmaceutically acceptable salt thereof, for preparing a medicinal product for treating schizophrenia, and in particular acute episodes of schizophrenia. This use may be simultaneous, separated or spread out over time.

The present invention also relates to the method for treating a schizophrenic patient, and in particular during acute episodes of schizophrenia, which consists in administering a combination of cyamemazine and an a typical neuroleptic, or a pharmaceutically acceptable salt thereof, to the patient, either simultaneously or separately or in a manner spread out over time.

The doses depend on the desired effect, on the duration of treatment and on the route of administration used.

They are generally from 50 to 600 mg per day of cyamemazine. The doses of a typical neuroleptic are generally the doses recommended for single use. Thus, the dose will be from 1 to 20 mg per day of olanzapine, or else from 1 to 16 mg per day of risperidone, or else from 1 to 24 mg per day of sertindole, or else from 1 to 800 mg per day of quetiapine, or else from 20 to 160 mg per day of ziprasidone.

Preferably, the dose of olanzapine is from 5 to 20 mg/day, or else the dose of risperidone is from 4 to 8 mg/day, or else the dose of sertindole is from 2 to 8 mg/day, or else the dose of quetiapine is from 225 to 800 mg/day, or else the dose of ziprasidone is from 80 to 160 mg/day.

When two a typical neuroleptics are used in the combination, the doses of each one will be adjusted to obtain the desired effect.

In general, the physician will determine the suitable dose depending on the age, on the weight and on all the other factors specific to the subject to be treated.

What is claimed is:

1. A pharmaceutical composition comprising at least about 50 mg to about 600 mg of cyamemazine in combination with an atypical neuroleptic selected from the group consisting of olanzapine and risperidone, or a pharmaceutically acceptable salt thereof, optionally in combination with a pharmaceutically acceptable carrier.

2. The composition according to claim 1, wherein cyamemazine is present in an amount of from about 100 mg to about 500 mg.

3. The composition according to claim 2 wherein the atypical neuroleptic is olanzapine.

4. The composition according to claim 2 wherein the atypical neuroleptic is risperidone.

5. The composition according to claim 1 wherein the atypical neuroleptic is olanzapine.

6. The composition according to claim 1 wherein the atypical neuroleptic is risperidone.

7. The composition according to claim 1, wherein cyamemazine and the atypical neuroleptic are in pure state or in the presence of any compatible and pharmaceutically acceptable diluent or adjuvant.

8. A method for preparing a composition as defined in claim 1 comprising the step of mixing at least about 50 mg of cyamemazine with a suitable amount of an atypical neuroleptic or a pharmaceutically acceptable salt thereof, optionally in combination with a pharmaceutically acceptable carrier.

9. A method for treating a patient suffering from schizophrenic disorders comprising administering to said patient an effective amount of a combination of cyamemazine and an atypical neuroleptic selected from the group consisting of olanzapine and risperidone, or a pharmaceutically acceptable salt thereof, optionally in combination with a pharmaceutically acceptable carrier.

10. The method according to claim 9 wherein cyamemazine is present in an amount of from about 50 mg to about 600 mg.

11. The method according to claim 9 wherein the atypical neuroleptic is olanzapine.

12. The method according to claim 9, wherein the atypical neuroleptic is risperidone.

13. The method according to claim 9 wherein the patient is suffering from acute episodes of schizophrenia.

14. A method for treating a patient suffering from schizophrenic disorders comprising administering to said patient an effective amount of a combination of cyamemazine and an atypical neuroleptic selected from the group consisting of olanzapine and risperidone or a pharmaceutically acceptable salt thereof, optionally in combination with a pharmaceutically acceptable carrier.

* * * * *